United States Patent [19]

Wilson

[11] Patent Number: 5,659,054
[45] Date of Patent: Aug. 19, 1997

[54] PREPARATION OF MONOCYCLOPENTADIENYL METAL COMPLEXES BY NUCLEOPHILIC SUBSTITUTION OF BIS (CYCLOPENTADIENYL) METAL COMPLEXES

[75] Inventor: David R. Wilson, Midland, Mich.

[73] Assignee: The Dow Chemical Company, Midland, Mich.

[21] Appl. No.: 469,192

[22] Filed: Jun. 6, 1995

Related U.S. Application Data

[62] Division of Ser. No. 209,344, Mar. 14, 1994, Pat. No. 5,504,224.

[51] Int. Cl.$^6$ ........................................... C07F 7/08
[52] U.S. Cl. ................... 556/7; 556/9; 556/11; 556/12; 556/19; 556/20; 556/28; 556/53; 556/54; 556/56; 502/152; 502/155; 526/160; 526/943
[58] Field of Search .................. 556/7, 9, 11, 12, 556/20, 19, 28, 53, 54, 56

[56] References Cited

U.S. PATENT DOCUMENTS 5,026,798   6/1991   Canich ..................................... 502/127

FOREIGN PATENT DOCUMENTS

| | | |
|---|---|---|
| 0416815 | 8/1990 | European Pat. Off. . |
| 0418044 | 9/1990 | European Pat. Off. . |
| 0514828 | 5/1992 | European Pat. Off. . |
| 3936096 | 10/1989 | Germany . |
| WO9200333 | 1/1992 | WIPO . |
| WO9319104 | 9/1993 | WIPO . |

OTHER PUBLICATIONS

Zeitschrift fur Naturforschung, vol. 44b, pp. 1593–1598 1989.
Journal of Organometallic Chemistry, vol. 231, 1982, pp. C43–C48.
Chemical Abstracts, vol. 121, No. 9, 29 Aug. 1994, Colombus, Ohio, US; abstract No. 109063r.
J. Organometal. Chem., 110, pp. 321–326 (1976).
Organometallics, 12, pp. 1936–1945 (1993).
Organometallics, 10, pp. 2665–2671 (1991).

*Primary Examiner*—David W. Wu

[57] ABSTRACT

Bridged monocyclopentadienyl derivatives of a Group 4 metal are prepared by contacting a corresponding bis (cyclopentadienyl) metal complex with an alkali metal derivative or alkaline earth metal derivative of a hydrocarbyl ligand R, which is optionally substituted with one or more amino, phosphino, ether, thioether, or silyl groups. The bis(cyclopentadienyl) Group 4 metal complexes can be prepared by contacting a compound corresponding to one of the formulas $(Cp)_3MQ_nX_r$, $(Cp)_2MQ_nX_{r+1}$, or $CpMQ_nX_{r+2}$ and a dianionic salt compound corresponding to the formula: $(L^{+x})_y(Cp^*\text{-}Z\text{-}Y)^{-2}$ or $((LX')^{+x})_y(Cp^*\text{-}Z\text{-}Y)^{-2}$. An addition polymerization catalyst comprising a bis(cyclopentadienyl) Group 4 metal complex and an activating cocatalyst, and an addition polymerization process using such a catalyst.

8 Claims, No Drawings

PREPARATION OF MONOCYCLOPENTADIENYL METAL COMPLEXES BY NUCLEOPHILIC SUBSTITUTION OF BIS (CYCLOPENTADIENYL) METAL COMPLEXES

CROSS-REFERENCE TO RELATED APPLICATION

This is a divisional of application Ser. No., 08/209,344 filed Mar. 14, 1994, now U.S. Pat. No. 5,504,224.

BACKGROUND OF THE INVENTION

This invention relates to a process for preparing certain bridged monocyclopentadienyl Group 4 metal complexes. More particularly, this invention relates to such a process involving nucleophilic substitution of corresponding bis (cyclopentadienyl) Group 4 metal complexes. Further, the invention relates to bis(cyclopentadienyl) Group 4 metal complexes, to a process for preparing the same, and to an addition polymerization process using a catalyst comprising the same complex and an activating cocatalyst.

Monocyclopentadienyl Group 4 metal complexes, particularly those wherein the cyclopentadienyl derivative group is part of a bridging ligand group are known and useful in catalyst compositions for addition polymerizations, particularly in polymerizing and interpolymerizing olefins, diolefins, vinyl-aromatic monomers, and/or acetylenically unsaturated monomers.

Bridged monocyclopentadienyl Group 4 metal complexes, including those which also contain at least one hydrocarbon group other than a cyclopentadienyl covalently bonded to the Group 4 metal, are disclosed in EP-A-0,416, 815, EP-A-0,418,044, U.S. Pat. No. 5,026,798, WO 92/00333 and WO 93/19104 (corresponding to U.S. Ser. No. 8003, filed Jan. 21, 1993 U.S. Pat. No. 5,374,696).

EP-A-0,418,044, in example 3 and WO 92/00333 teach that bridged monocyclopentadienyl dihydrocarbyl Group 4 metal(+4) complexes can be prepared by hydrocarbylating the corresponding bridged monocyclopentadienyl Group 4 metal(+4) dihalide complexes with a Grignard, lithium, sodium or potassium salt of the hydrocarbyl ligand. The dihalide complexes in themselves are prepared by reacting the Group 4 metal(+4) tetrahalide with a dianionic derivative of the bridging monocyclopentadienyl ligand. Alternative methods to prepare these dihalide complexes are disclosed in EP-A-0,416,815 and EP-A-0,514,828 which require reacting an ether adduct of a transition metal(+3) trihalide compound with the dianionic derivative of the cyclopentadienyl ligand, followed by contacting the resulting complex with a non-interfering oxidizing agent, such as for example AgCl (EP-A-0,416,815) or an organic halide (EP-A-0,514, 828) to raise the oxidation state of the metal to form the desired metal(+4) dihalide complex.

The bridged monocyclopentadienyl mono-hydrocarbyl metal(+3) coordination complexes can be prepared by hydrocarbylating the corresponding bridged monocyclopentadienyl metal(+3) monohalide coordination complexes with a Grignard, lithium, sodium or potassium salt of the hydrocarbyl ligand. The bridged mono-cyclopentadienyl metal(+3) monohalide complexes themselves are prepared by reacting a Group 4 metal(+3) trihalide compound, in the form of an ether adduct, with a dianionic derivative of the bridging monocyclopentadienyl ligand. Alternatively, the bridged monocyclopentadienyl monohydrocarbyl metal(+3) complexes are prepared by monohydrocarbylating the corresponding bridged monocyclopentadienyl metal(+4) dihalide complexes with a Grignard, lithium, sodium or potassium salt of the hydrocarbyl ligand, followed by reducing with a metal such as magnesium. These synthesis methods are described in WO 93/19104 (corresponding to U.S. Ser. No. 8003, filed Jan. 21, 1993).

All of the synthesis methods described hereinbefore start from Group 4 metal tri- or tetrahalide compounds which are corrosive, toxic, and air and moisture sensitive. In the presence of moisture these compounds liberate HCl. In order to facilitate handling thereof, prior to the reaction step the transition metal tri- or tetrahalide compound is typically converted to its ether-adduct in a separate step with, for example, THF or diethyl ether. This adduct formation step in itself is difficult to perform on a large scale due to the high exothermicity of the reaction, requiring efficient cooling and low to very low temperatures and careful addition to prevent Lewis acid-catalyzed cleavage of the ether molecule, and inert atmosphere. The adduct is usually recovered before it is reacted with the dianionic derivative of the bridged monocyclopentadienyl ligand compound.

In J. Organometal. Chem. 1976, 110, 321, A. Dormond et al. describe the reaction between bis(cyclopentadienyl) titanium(+4) dichloride and a dianionic derivative of a bridged biscyclopentadienyl ligand, $Na_2[C_5H_4(CH_2)_3C_5H_4]$, to form a mixture of $[di-\eta^5-C_5H_4(CH_2)_3C_5H_4]Ti(\eta^1-C_5H_5)_2$ and $(\eta^5-C_5H_5)_2Ti[di-\eta^1-C_5H_4(CH_2)_3C_5H_4]$. Dormond et al. further disclose that bis(cyclopentadienyl) titanium(+4) bis(phenyl) when attacked by phenyl lithium forms the complex $[Cp_2TiPh_3]^-Li^+$ which ultimately decomposes to $CpTiPh_2$, CpLi and a phenyl radical.

DE-A-3,936,096 generically discloses the reaction between $MeX'_q.(solv')_r$, wherein Me could be Ti or Zr, X' could be Cl, Br, I, —OOCR', —OR', —NR'$_2$, -cyclopentadienyl, solv' is ether or tert. amine, q is 2–5, and r is 0–3, with a dialkali metal- or digrignard organo compound to form homoleptic metallacyclic organometal compounds.

It would be desirable to develop an improved process to prepare mono- or dihydrocarbyl derivatives bridged monocyclopentadienyl Group 4 metal complexes which process avoids the use of the corrosive, toxic, and air and moisture sensitive metal tetrahalide or trihalide starting compounds, and avoids the formation of an ether adduct.

It would also be desirable to provide a process for the preparation of monohydrocarbyl derivatives of bridged monocyclopentadienyl Group 4 metal(+3) complexes which process avoids the use of any Group 4 metal(+4) compound or complex and thus requires fewer steps, such as a reduction step from the +4 oxidation state to the +3 oxidation state.

It would yet further be desirable to provide certain novel stable bis(cyclopentadienyl) metal complexes which enable the desired mono- or dihydrocarbyl derivatives of bridged monocyclopentadienyl Group 4 metal complexes to be prepared. It would be furthermore desirable to provide certain novel stable bis(cyclopentadienyl) metal complexes which are useful in catalyst compositions for addition polymerization processes.

SUMMARY OF THE INVENTION

Surprisingly, it has been found that bridged mono- and dihydrocarbyl derivatives of monocyclopentadienyl Group 4 metal complexes can be prepared by nucleophilic substitution of corresponding bis(cyclopentadienyl) metal complexes.

According to the present invention there is provided a process for the preparation of a monocyclopentadienyl metal complex corresponding to the formula:

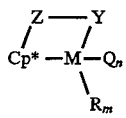 (I)

wherein:

Cp* is a cyclopentadienyl group or a substituted derivative of said cyclopentadienyl group wherein the substituent is a hydrocarbyl, silyl, amino, aminohydrocarbyl, halo, halohydrocarbyl, silylhydrocarbyl, hydrocarbylmetalloid or halohydrocarbylmetalloid, said Cp* being covalently bonded to Z and π-bonded to M and containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms and being covalently bonded to Y and Cp*;

Y is a linking group comprising nitrogen, phosphorus, oxygen or sulfur covalently bonded to M and Z through said nitrogen, phosphorus, oxygen or sulfur atom;

M is a metal of Group 4 of the Periodic Table of the Elements in an oxidation state of +3 or +4;

R independently each occurrence is a hydrocarbyl group, optionally substituted with one or more amino, phosphino, ether, thioether, or silyl groups, said R having up to 50 nonhydrogen atoms, provided that R is not a cyclopentadienyl group or substituted cyclopentadienyl group;

Q independently each occurrence is hydride, or a monovalent anionic ligand selected from hydrocarbyl, silyl, amido and phosphido groups, said groups optionally being further substituted with one or more amino, phosphino, ether, ester, thioether, or silyl groups, said Q having up to 50 nonhydrogen atoms, provided that Q is not a cyclopentadienyl group or substituted cyclopentadienyl group; and m is 1 or 2; n is 0 or 1; and the sum of m and n is two less than the oxidation state of M;

the process comprising contacting in an aprotic solvent:

1) a bis(cyclopentadienyl) Group 4 metal complex corresponding to the formula:

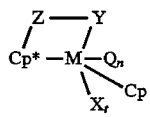 (II)

wherein:

Cp independently is a cyclopentadienyl group or a substituted derivative of said cyclopentadienyl group wherein the substituent is hydrocarbyl, silyl, halo, amino, aminohydrocarbyl, halohydrocarbyl, silylhydrocarbyl, hydrocarbylmetalloid or halohydrocarbylmetalloid, said Cp being π-bonded to M, and containing up to 50 nonhydrogen atoms;

X independently each occurrence is halo, hydrocarbyloxy, siloxy, carboxy, sulfido or sulfonato;

Cp*, Z, Y, M, Q, and n are as previously defined; and t is 0 or 1; and the sum of n and t is three less than the oxidation state of M; and 2) an alkali metal derivative or alkaline earth metal derivative of R, wherein R is as previously defined, to form the monocyclopentadienyl complex of formula (I).

According to another aspect the present invention provides a bis(cyclopentadienyl) Group 4 metal complex corresponding to the formula:

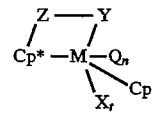 (II)

wherein:

Cp* is a cyclopentadienyl group or a substituted derivative of said cyclopentadienyl group wherein the substituent is a hydrocarbyl, silyl, amino, aminohydrocarbyl, halo, halohydrocarbyl, silylhydrocarbyl, hydrocarbylmetalloid or halohydrocarbylmetalloid, said Cp* being covalently bonded to Z and π-bonded to M and containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms and being covalently bonded to Y and Cp*, with the proviso that when M is zirconium then Z is not 1,2-ethene-diyl or 1,3-propanediyl;

Y is a linking group comprising nitrogen, phosphorus, oxygen or sulfur covalently bonded to M and Z through said nitrogen, phosphorus, oxygen or sulfur atom;

M is a metal of Group 4 of the Periodic Table of the Elements in an oxidation state of +3 or +4;

X independently each occurrence is halo, hydrocarbyloxy, siloxy, carboxy, sulfido or sulfonato;

Cp independently is a cyclopentadienyl group or a substituted derivative of said cyclopentadienyl group wherein the substituent is hydrocarbyl, silyl, halo, amino, aminohydrocarbyl, halohydrocarbyl, silylhydrocarbyl, hydrocarbylmetalloid or halohydrocarbylmetalloid, said Cp being π-bonded to M, and containing up to 50 nonhydrogen atoms;

Q independently each occurrence is hydride, or a monovalent anionic ligand selected from hydrocarbyl, silyl, amido and phosphido groups, said groups optionally being further substituted with one or more amino, phosphino, ether, ester, thioether, or silyl groups, said Q having up to 50 nonhydrogen atoms, provided that Q is not a cyclopentadienyl group or substituted cyclopendienyl group;

n is 0 or 1; t is 0 or 1; and the sum of n and t is three less than the oxidation state of M.

According to yet a further aspect the present invention provides a process for preparing bis(cyclopentadienyl) Group 4 metal complexes corresponding to the formula:

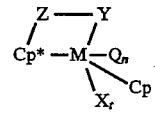 (II)

wherein:

Cp* is a cyclopentadienyl group or a substituted derivative of said cyclopentadienyl group wherein the substituent is a hydrocarbyl, silyl, amino, aminohydrocarbyl, halo, halohydrocarbyl, silylhydrocarbyl, hydrocarbylmetalloid or halohydrocarbylmetalloid, said Cp* being covalently bonded to Z and π-bonded to M and containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms and being covalently bonded to Y and Cp*;

Y is a linking group comprising nitrogen, phosphorus, oxygen or sulfur covalently bonded to M and Z through said nitrogen, phosphorus, oxygen or sulfur atom;

M is a metal of Group 4 of the Periodic Table of the Elements in an oxidation state of +3 or +4;

Q independently each occurrence is hydride, or a monovalent anionic ligand selected from hydrocarbyl, silyl, amido and phosphido groups, said groups optionally being further substituted with one or more amino, phosphino, ether, ester, thioether, or silyl groups, said Q having up to 50 nonhydrogen atoms, provided that Q is not a cyclopentadienyl group or a substituted cyclopentadienyl group;

Cp independently is a cyclopentadienyl group or a substituted derivative of said cyclopentadienyl group wherein the substituent is hydrocarbyl, silyl, halo, amino, aminohydrocarbyl, halohydrocarbyl, silylhydrocarbyl, hydrocarbylmetalloid or halohydrocarbylmetalloid, said Cp being π-bonded to M, and containing up to 50 nonhydrogen atoms;

X independently each occurrence is halo, hydrocarbyloxy, siloxy, carboxy, sulfido or sulfonato;

n is 0 or 1; t is 0 or 1; and the sum of n and t is three less than the oxidation state of M;

the process comprising contacting in an aprotic organic solvent: i) a compound corresponding to one of the formulas $(Cp)_3MQ_nX_t$, $(Cp)_2MQ_nX_{t+1}$, or $CpMQ_nX_{t+2}$ or a neutral Lewis base coordinated adduct thereof, wherein: n is 0 or 1; t is 0 or 1; the sum of n and t is three less than the valence of M; and Cp, M, Q and X are as previously defined; and ii) a dianionic salt compound corresponding to the formula: $(L^{+x})_y(Cp^*-Z-Y)^{-2}$ or $((LX')^{+x})_y(Cp^*-Z-Y)^{-2}$ wherein L is a metal of Group 1 or 2 of the Periodic Table of the Elements; X' independently is chloro, bromo, or iodo; x is 1 or 2, y is 1 or 2, and the product of x and y equals 2; and Cp*, Z, and Y are as previously defined; to form the complex of formula (II).

According to a further aspect, the present invention provides an addition polymerization catalyst composition comprising a bis(cyclopentadienyl) Group 4 metal coordination complex as described hereinbefore and an activating cocatalyst.

According to another aspect, the present invention provides a process for addition polymerization of one or more addition polymerizable monomers, wherein a catalyst composition as described hereinbefore is contacted with one or more addition polymerizable monomers under conditions promoting addition polymerization.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The recitation "metalloid", as used herein, refers to boron, phosphorus, silicon, germanium, and arsenic.

Generally, the Group 4 metal is titanium, zirconium, or hafnium. Preferably it is titanium or zirconium, and most preferably titanium.

Each of up to four of the five carbon atoms making up the five membered ring in the cyclopentadienyl Cp* group independently may be unsubstituted or substituted with the same or a different radical selected from the group consisting of hydrocarbyl radicals, halogen radicals, silyl radicals, amino radicals, substituted hydrocarbyl radicals wherein one or more hydrogen atoms are replaced by a halogen atom, amino radical or silyl radicals, hydrocarbyl-substituted metalloid radicals, and halohydrocarbyl-substituted metalloid radicals. Preferred hydrocarbyl and substituted hydrocarbyl radicals contain from 1 to 20 carbon atoms and include linear, branched, cyclic, or alkyl-substituted cyclic, aliphatic hydrocarbon radicals, aromatic radicals and alkyl-substituted aromatic radicals. Suitable hydrocarbyl-substituted metalloid radicals include mono-, di- and trihydrocarbyl substituted metalloid radicals wherein each of the hydrocarbyl groups contains from 1 to about 20 carbon atoms. More particularly, suitable hydrocarbyl-substituted metalloid radicals include trimethylsilyl, triethylsilyl, ethyldimethylsilyl, methyldiethylsilyl, triphenylgermyl, trimethylgermyl and the like. Adjacent substituents in the cyclopentadienyl Cp* may be linked together thereby forming an indenyl, tetrahydroindenyl, fluorenyl, tetrahydrofluorenyl, or octahydrofluorenyl group in place of the cyclopentadienyl group.

The bridging monocyclopentadienyl ligand moiety consisting of -Cp*-Z-Y- is a dianionic ligand having ionic charges residing formally on Cp* and Y. Such ligand causes the resulting complex to possess unique properties about the active metal catalyst site resulting in highly active Group 4 metal catalysts. These ligands and complexes containing the same are further described in U.S. patent application Ser. No. 545,403, filed Jul. 3, 1990, (corresponding to EP-A-0, 416,815) and U.S. Ser. No. 8003, filed Jan. 21, 1993 (corresponding to WO 93/19104) which are incorporated herein by reference.

Q independently each occurrence preferably is: hydride; primary, secondary or tertiary alkyl; aryl; aralkyl; trialkyl-silylalkyl; alkoxyalkyl; alkyl(polyalkyleneoxy)alkyl; dialkylaminoalkyl; dialkylaminoaralkyl; allyl; alkyl-substituted allyl; alkadienyl; alkyl-substituted alkadienyl; dialkylphosphinoalkyl; or dialkylphosphinoaralkyl, said Q having up to 20 nonhydrogen atoms. More preferably Q is a hydrocarbyl of up to 20 carbons.

Q may be present in the bis(cyclopentadienyl) complex of formula (II). Usually, Q will not be replaced by R when the complex of formula (II) is contacted with the nucleophilic reacTant, i.e., the alkali metal derivative or alkaline earth metal derivative of ligand R. The substituent X which may be present in the complex of formula (II), however, will be replaced by said nucleophilic reactant when contacted with the nucleophilic reactant.

In general R independently each occurrence is a covalently bonded hydrocarbyl group, optionally substituted with one or more amino, phosphino, ether, thioether, or silyl groups, said R having up to 50 nonhydrogen atoms, provided that R is not a cyclopentadienyl group or substituted cylcopentadienyl group. Preferably R is: primary, secondary or tertiary alkyl; aryl; aralkyl; trialkylsilylalkyl; alkoxyalkyl; alkyl(polyalkyleneoxy)alkyl; dialkylaminoalkyl; diatkylaminoaralkyl; allyl; alkyl-substituted allyl; alkadienyl;

alkyl-substituted alkadienyl; dialkylphosphinoalkyl; or dialkylphosphinoaralkyl, said R having up to 20 nonhydrogen atoms. Most preferably R is hydrocarbyl of up to 20 carbons.

X preferably is halide, especially chloride, or alkoxide or aryloxide, preferably a $C_{1-8}$ alkoxide such as for example methoxide, ethoxide, isopropoxide, n- and tert-butoxide.

Cp in the complex of formula (II) is a cyclopentadienyl group π-bonded to M or is a cyclopentadienyl group π-bonded to M which is substituted with one or more of the same or different radicals selected from the group consisting of amino radicals, halogen radicals, hydrocarbyl radicals, substituted-hydrocarbyl radicals wherein one or more hydrogen atoms is replaced by a halogen atom or a silyl group, an amino radical, hydrocarbyl-substituted metalloid radicals, and halohydrocarbyl-substituted metalloid radicals. Adjacent substituents in the cyclopentadienyl Cp may be linked together thereby forming an indenyl, tetrahydroindenyl, fluorenyl, tetrahydrofluorenyl, or octahydrofluorenyl group in place of the cyclopentadienyl group.

According to the present process more preferably a monocyclopentadienyl complex corresponding to the formula:

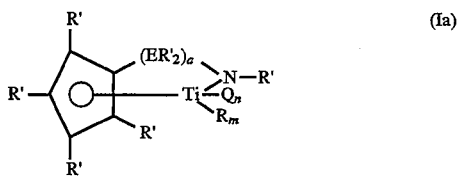

(Ia)

wherein:

R' each occurrence is independently selected from the group consisting of hydrogen, silyl, hydrocarbyl, or silyl-substituted hydrocarbyl having up to 10 carbon or silicon atoms;

E independently each occurrence is silicon or carbon;

Q is allyl, alkyl-substituted allyl, pentadienyl, alkyl-substituted pentadienyl, or an alkyl, aryl, aralkyl, silyl, trialkylsilylalkyl, or dialkylaminoaralkyl group, said group having up to 10 carbons;

R is allyl, alkyl-substituted allyl, pentadienyl, alkyl-substituted pentadienyl, or an alkyl, aryl, aralkyl, silyl, trialkylsilylalkyl, or dialkylaminoaralkyl group, said group having up to 10 carbons; and a is 1 or 2; m is 1 or 2; n is 0 or 1; and the sum of m and n is two less than the oxidation state of titanium;

is prepared by contacting:

1) a bis(cyclopentadienyl) Group 4 metal complex corresponding to the formula:

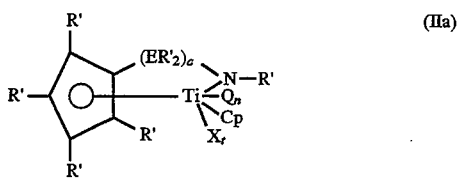

(IIa)

wherein:
R', E, Q, n, and a are as previously defined;
t is 0 or 1;
X and Cp are as defined for formula (II); and the sum of n and t is three less than the oxidation state of titanium; and 2) the alkali metal derivative or alkaline earth metal derivative of ligand R.

Preferably R' on the foregoing cyclopentadienyl groups each occurrence is hydrogen, methyl, ethyl, propyl, butyl, pentyl, hexyl, including isomers of these radicals, norbornyl, benzyl, phenyl, or two such R' groups together are a $C_3$ or $C_4$ hydrocarbylene moiety forming a fused ring with adjacent carbons of the cyclopentadienyl group.

In the bridged monocyclopentadienyl complexes of formula (I) or (Ia), preferably m is 1 or 2 and n is 0. These are prepared from the corresponding bis(cyclopentadienyl) complexes of formula (II) or (IIa) wherein preferably n is 0, and t is 0 or 1.

Highly preferred bridged monocyclopentadienyl complexes of formula (I) or (Ia) are those wherein m is 1 and n is 0. These are the Group 4 metal complexes, and especially the titanium complexes, having a +3 oxidation state. These are prepared from the corresponding bis(cyclopentadienyl) complexes of formula (II) or (IIa) wherein n is 0, and t is 0.

The present process, especially in combination with the preferred process to make the bis(cyclopentadienyl) Group 4 metal complexes of formulas (II) and (IIa), which will be described in more detail hereinafter, is capable of preparing the bridged monocyclopentadienyl Group 4 metal monohydrocarbyl complexes in the +3 oxidation state in good yield while avoiding Group 4 metal tri- or tetrahalide starting compounds and the reduction step which would be required when starting from a Group 4 metal compound in the +4 oxidation state.

It has been found highly desirable when M is Ti(+3), that R should be capable of stabilizing the resulting complex. Exemplary R groups capable of stabilizing the resulting complex are ligands comprising an amino, phosphino, ether or thioether functionality capable of forming a coordinate-covalent bond or chelating bond with Ti, or comprising an ethylenic unsaturation capable of forming a η-bond, more particularly an η3 or η5 bond, with Ti. R preferably is allyl or alkyl-substituted allyl, alkadienyl or alkyl-substituted alkadienyl all of which are π-bonded to M, or amino-, phosphino- or alkoxy-substituted hydrocarbyl of up to 20 carbon atoms. More preferably R is an alkyl-substituted allyl, alkyl-substituted pentadienyl both of which are π-bonded to M, or dialkyl-aminoaralkyl group, most preferably 2-(N,N-dimethylamino)benzyl. The stabilizing R groups are further described in U.S. Ser. No. 8003, filed Jan. 21, 1993 (corresponding to WO 93/19104).

In the bis(cyclopentadienyl) complexes of formula (II) or (IIa) Cp is preferably cyclopentadienyl or a $C_{1-6}$ substituted cyclopentadienyl.

Examples of the above highly preferred Group 4 metal complexes of formula (Ia) include compounds wherein the R' on the amido group is methyl, ethyl, propyl, butyl, pentyl, hexyl, including isomers of these radicals, norbornyl, benzyl, phenyl, etc.; the cyclopentadienyl group (including R' substituents) is cyclopentadienyl, tetramethylcyclopentadienyl, indenyl, tetrahydroindenyl, fluorenyl, octahydrofluorenyl, etc.; and R is methyl, neopentyl, trimethylsilyl, trimethylsilylmethyl, norbornyl, benzyl, methylbenzyl, phenyl, 2-(N,N-dimethylamino) benzyl, allyl, 2-methylpentadienyl, 2,4-dimethylpentadienyl, etc. When R is allyl, substituted allyl, pentadienyl, or substituted pentadienyl and the Group 4 metal complex is in the +3 oxidation state, then R is π-bonded to M.

Specific titanium(+3) complexes of formula (Ia) that can be prepared according to the present process include: [(tert-butylamido)(η$^5$-cyclopentadienyl)-1,2-ethanediyl]titanium 2-(N,N-dimethylamino)benzyl, [(tert-butylamido)(tetramethyl-η$^5$-cyclopentadienyl)-1,2-ethanediyl]titanium 2-(N,N-dimethylamino)benzyl, [(tert-butylamido)(ethyl-η$^5$- cyclopentadienyl)-1,2-ethanediyl]titanium 2-(N,N-dimethylamino)benzyl, [(methylamido)(tetramethyl-η$^5$-cyclopentadienyl)-1,2-ethanediyl]titanium 2-(N,N-dimethylamino)benzyl, [(methylamido)(η$^5$-cyclopentadienyl)-1,2-ethanediyl]titanium 2-(N,N-dimethylamino)benzyl, [(methylamido)(ethyl-η$^5$-cyclopentadienyl)-1,2-ethanediyl]titanium 2-(N,N-dimethylamino)benzyl, [(tert-butylamido)(η$^5$-cyclopentadienyl)-1,2-ethanediyl]titanium allyl, [(tert-butylamido)(tetramethyl-η$^5$-cyclopentadienyl)-1,2-ethanediyl]titanium allyl, [(tert-butylamido)(ethyl-η$^5$-cyclopentadienyl)-1,2-ethanediyl]titanium allyl, [(methylamido)(tetramethyl-η$^5$-cyclopentadienyl)-1,2-ethanediyl]titanium allyl, [(methylamido)(η$^5$-cyclopentadienyl)-1,2-ethanediyl]titanium allyl, [(methylamido)(ethyl-η$^5$-cyclopentadienyl)-1,2-ethanediyl]titanium allyl, [(phenylamido)(ethyl-η$^5$-cyclopentadienyl)-1,2-ethanediyl]titanium methyl, [(tert-butylamido)(η$^5$-cyclopentadienyl)-1,2-ethanediyl]titanium 2-(dimethylphosphino)benzyl, [(tert-butylamido)(tetramethyl-η$^5$-cyclopentadienyl)-1,2-ethanediyl]titanium 2-(dimethylphosphino)benzyl, [(tert-butylamido)(ethyl-η$^5$-cyclopentadienyl)-1,2-ethanediyl]titanium 2-(dimethylphosphino)benzyl, [(methylamido)(tetramethyl-η$^5$-cyclopentadienyl)-1,2-ethanediyl]titanium 2-(dimethylphosphino)benzyl, [(methylamido)(η$^5$-cyclopentadienyl)1,2-ethanediyl]titanium 2-(dimethylphosphino)benzyl, [(methylamido)(ethyl-η$^5$-cyclopentadienyl)-1,2-ethanediyt]titanium 2-(dimethylphosphino)benzyl, [(tert-butylamido)(η$^5$-cyclopentadienyl)-1,2-ethanediyl]titanium 2-(N,N-bis(pentafluorophenyl)amino)benzyl, [(tert-butylamido)(tetramethyl-η$^5$-cyclopentadienyl)-1,2-ethanediyl]titanium 2-(N,N-bis(trimethylsilyl)amino)benzyl, [(tert-butylamido)(η$^5$-cyclopentadienyl)dimethylsilane]titanium 2-(N,N-dimethylamino)benzyl, [(tert-butylamido)(tetramethyl-η$^5$-cyclopentadienyl)dimethylsilane]titanium 2-(N,N-dimethylamino)benzyl, [(tert-butylamido)(ethyl-η$^5$-cyclopentadienyl)dimethylsilane]titanium 2-(N,N-dimethylamino)benzyl, [(methylamido)(tetramethyl-η$^5$-cyclopentadienyl)dimethylsilane]titanium 2-(N,N-dimethylamino)benzyl, [(methylamido)(η$^5$-cyclopentadienyl)dimethylsilane]titanium 2-(N,N-dimethylamino)benzyl, [(methylamido)(ethyl-η$^5$-cyclopentadienyl)dimethylsilane]titanium 2-(N,N-dimethylamino)benzyl, [(tert-butylamido)(η$^5$-cyclopentadienyl)dimethylsilane]titanium allyl, [(tert-butylamido)(tetramethyl-η$^5$-cyclopentadienyl)dimethylsilane]titanium allyl, [(tert-butylamido)(ethyl-η$^5$-cyclopentadienyl)dimethylsilane]titanium allyl, [(methylamido)(tetramethyl-η$^5$-cyclopentadienyl)dimethylsilane]titanium allyl, [(methylamido)(η$^5$-cyclopentadienyl)dimethylsilane]titanium allyl, [(methylamido)(ethyl-η$^5$-cyclopentadienyl)dimethylsilane]titanium allyl, [(tert-butylamido)(η$^5$-cyclopentadienyl)dimethylsilane]titanium 2-(dimethylphosphino)benzyl, [(tert-butylamido)(tetramethyl-η$^5$-cyclopentadienyl)dimethylsilane]titanium 2-(dimethylphosphino)benzyl, [(tert-butylamido)(η$^5$-cyclopentadienyl)dimethylsilane]titanium 2-(N,N-bis(pentafluorophenyl)amino)benzyl, [(tert-butylamido)(tetramethyl-η$^5$-cyclopentadienyl)dimethylsilane]titanium 2-(N,N-bis(pentafluorophenyl)amino)benzyl, and [(methylamido)(ethyl-η5-cyclopentadienyl)dimethylsilane]titanium 2-(N,N-bis(trimethylsilyl)amino)benzyl, and the like.

Specific titanium(+4) complexes of formula (Ia) that can be prepared according to the present process include: [(tert-butylamido)(η$^5$-cyclopentadienyl)-1,2-ethanediyl]titanium dimethyl, [(tert-butylamido)(tetramethyl-η$^5$-cyclopentadienyl)-1,2-ethanediyl]titanium dibenzyl, [(methylamido)(tetramethyl-η$^5$-cyclopentadienyl)-1,2-ethanediyl]titanium (methyl) 2-(N,N-dimethylamino)benzyl, [(methylamido)(η$^5$-cyclopentadienyl)-1,2-ethanediyl]titanium dimethyl, [(methylamido)(ethyl-η$^5$-cyclopentadienyl)-1,2-ethanediyl]titanium (benzyl) 2-(N,N-dimethylamino)benzyl, [(tert-butylamido)(η$^5$-cyclopentadienyl)-1,2-ethanediyl]titanium (methyl)allyl, [(tert-butylamido)(tetramethyl-η$^5$-cyclopentadienyl)-1,2-ethanediyl]titanium dimethyl, [(tert-butylamido)(ethyl-η$^5$-cyclopentadienyl)-1,2-ethanediyl]titanium dibenzyl, [(methylamido)(tetramethyl-η$^5$-cyclopentadienyl)-1,2-ethanediyl]titanium (benzyl)allyl, [(phenylamido)(ethyl-η$^5$-cyclopentadienyl)-1,2-ethanediyl]titanium dimethyl, [(tert-butylamido)(η$^5$-cyclopentadienyl)-1,2-ethanediyl]titanium dibenzyl, [(phenylamido)(tetramethyl-η$^5$-cyclopentadienyl)-1,2-ethanediyl]titanium (2-(dimethylphosphino)benzyl) allyl, [(tert-butylamido)(ethyl-η$^5$-cyclopentadienyl)-1,2-ethanediyl]titanium (methyl) 2-(dimethylphosphino)benzyl, [(methylamido)(tetramethyl-η$^5$-cyclopentadienyl)-1,2-ethanediyl]titanium (benzyl) 2-(dimethylphosphino)benzyl, [(methylamido)(ethyl-η$^5$-cyclopentadienyl)-1,2-ethanediyl]titanium dibenzyl, [(tert-butylamido)(η$^5$-cyclopentadienyl)-1,2-ethanediyl]titanium (methyl) 2-(N,N-bis(pentafluorophenyl)amino)benzyl, [(tert-butylamido)(η$^5$-cyclopentadienyl)-1,2-ethanediyl]titanium (phenyl) 2-(N,N-dimethylamino)benzyl, [(tert-butylamido)(tetramethyl-η$^5$-cyclopentadienyl)-1,2-ethanediyl]titanium (methyl) 2-(N,N-bis(trimethylsilyl)amino)benzyl, [(tert-butylamido)(η$^5$-cyclopentadienyl)dimethylsilane]titanium dibenzyl, [(tert-butylamido)(tetramethyl-η$^5$-cyclopentadienyl)dimethylsilane]titanium dibenzyl, [(tert-butylamido)(ethyl-η$^5$-cyclopentadienyl)dimethylsilane]titanium (methyl) 2-(N,N-dimethylamino)benzyl, [(methylamido)(tetramethyl-η$^5$-cyclopentadienyl)dimethylsilane]titanium dimethyl, [(methylamido)(η$^5$-cyclopentadienyl)dimethylsilane]titanium dibenzyl, [(methylamido)(ethyl-η$^5$-cyclopentadienyl)dimethylsilane]titanium (benzyl) methyl, [(tert-butylamido)(η$^5$-cyclopentadienyl)dimethylsilane]titanium (allyl) benzyl, [(tert-butylamido)(tetramethyl-η$^5$-cyclopentadienyl)dimethylsilane]titanium (methyl) phenyl, [(tert-butylamido)(ethyl-η$^5$-cyclopentadienyl)dimethylsilane]titanium dimethyl, (methylamido)(tetramethyl-η$^5$-cyclopentadienyl)dimethylsilane]titanium (allyl) phenyl, [(methylamido)(η$^5$-cyclopentadienyl)dimethylsilane]titanium (methyl)allyl, [(methylamido)(ethyl-η$^5$-cyclopentadienyl)dimethylsilane]titanium dimethyl, [(tert-butylamido)(η$^5$-cyclopentadienyl)dimethylsilane]titanium (methyl) 2-(dimethylphosphino)benzyl, [(tert-butylamido)(tetramethyl-η$^5$-cyclopentadienyl)dimethylsilane]titanium (benzyl) 2-(dimethylphosphino)benzyl, [(tert-butylamido)(η$^5$-cyclopentadienyl)dimethylsilane]titanium (methyl) 2-(N,N-bis(pentafluorophenyl)amino)benzyl, [(tert-butylamido)(tetramethyl-η$^5$-cyclopentadienyl)dimethylsilane]titanium (methyl) 2-(N,N-bis(pentafluorophenyl)amino)benzyl, [(methylamido)(ethyl-η$^5$-cyclopentadienyl)dimethylsilane]titanium (methyl) 2-(N,N-bis(trimethylsilyl)amino)benzyl, and the like.

Other bridged monocyclopentadienyl Group 4 metal complexes that may be prepared according to the present invention will, of course, be apparent to those skilled in the art.

The alkali metal derivative or alkaline earth metal derivative of ligand R, i.e., the nucleophilic reactant, suitably is the lithium, Sodium, potassium, magnesium or magnesium halo (Grignard) salt of the group R. Preferably the alkali metal derivative or alkaline earth metal derivative of R is a compound of the formula LiR, MgR$_2$, or MgX"R, wherein R is as previously defined and X" is halogen, preferably chloro or bromo, most preferably chloro. Specific preferred examples of these nucleophilic reactants include: methyl lithium, benzyl lithium, phenyl lithium, 2-(N,N-dimethylamino)benzyl lithium, allyl lithium, 2-(dimethylphosphino)benzyl lithium, 2-(N,N-bis (pentafluorophenyl)amino)benzyl lithium, 2-(N,N-bis (trimethylsilyl)amino)benzyl lithium, methyl magnesium chloride, benzyl magnesium chloride, phenyl magnesium chloride, 2-(N,N-dimethylamino)benzyl magnesium chloride, allyl magnesium chloride, 2,4-dimethylpentadienyl potassium, pentadienyl lithium, 2-(dimethylphosphino)benzyl magnesium chloride, 2-(N,N-bis(pentafluorophenyl)amino)benzyl magnesium chloride, 2-(N,N-bis(trimethylsilyl)amino)benzyl magnesium chloride, and the like.

In general, the bridged monocyclopentadienyl complexes can be prepared by contacting the bis(cyclopentadienyl) metal complex and the nucleophilic reactant in a suitable aprotic organic solvent. The relative amounts of bis (cyclopentadienyl) metal complex and nucleophilic reactant used may vary considerably, however, the best yields are generally obtained when using a stoichiometric molar quantity, or a slight stoichiometric molar excess of the nucleophilic reactant. Accordingly, preferably from 0.95 to 1.2 molar equivalents of nucleophilic reactant are used per molar equivalent of Cp and X on M, more preferably from 1.0 to 1.1 molar equivalents.

Suitable reaction media lot the formation of the bridged monocyclopentadienyl complexes are hydrocarbons and ethers. Examples include straight and branched-chain hydrocarbons such as isobutane, butane, pentane, hexane, heptane, octane, and mixtures thereof; cyclic and alicyclic hydrocarbons such as cyclohexane, cyctoheptane, methylcyclohexane, methylcycloheptane, and mixtures thereof; aromatic and alkyl-substituted aromatic compounds such as benzene, toluene, xylene and the like; $C_{1-4}$ dialkyl ethers, $C_{1-4}$ dialkyl ether derivatives of (poly)alkylene glycols, and cyclic ethers such as tetrahydrofuran. Mixtures of the foregoing are also suitable. More preferably the aprotic solvent is selected from the group consisting of ethers and aliphatic, cycloaliphatic, aromatic and alkyl-aromatic hydrocarbons. Most preferably, the solvent is diethyl ether or tetrahydrofuran.

The process to prepare the bridged mono- cyclopentadienyl complexes is usually conducted at a temperature from −78° C. to 150° C., preferably between −25° C. and 100° C., most preferably between 0° C. and 50° C. The time of reaction may vary from a few minutes to several days, but is generally a few hours.

The recovery procedure for the bridged monocyclopentadienyl complexes involves separation from the resulting alkali metal or alkaline earth metal salt and from the reaction medium. Typically, the byproduct salts are the alkali metal or alkaline earth metal salts of Cp and X, if present in the bis(cyclopentadienyl) metal complex. The byproduct salts may be separated from the desired product by precipitation and filtration, extraction into a secondary solvent or other separation technique, depending of course on the differences between the solubility characteristics of both the desired product and byproduct salts. The recovery procedure is facilitated by the use of reaction media that are solvents for the resulting bridged monocyclopentadienyl complex but are non-solvents for the resulting byproducts, or vice versa.

A preferred example of such a solvent in which the desired product is soluble but the alkali metal or alkaline earth metal cyclopentadienide salt generally is not is hexane.

According to a preferred embodiment of the present process, and according to a further aspect of the present invention, a process is provided for the preparation of the bridged bis(cyclopentadienyl) Group 4 metal coordination complexes of formula (II) and (IIa) by contacting in an aprotic organic solvent: i) a compound corresponding to one of the formulas $(Cp_3)MQ_nX_t$, $(Cp)_2MQ_nX_{t+1}$, or $CpMQ_nX_{t+2}$ or a neutral Lewis base coordinated adduct thereof: wherein n is 0 or 1, t is 0 or 1, and the sum of n and t is three less than the oxidation state of M, wherein M, Cp, X, and Q are as previously defined; and ii) a dianionic salt compound corresponding to the formula: $(L^{+x})_y(Cp^*\text{-}Z\text{-}Y)^2$ or $((Lx')^{+x})_y(Cp^*\text{-}Z\text{-}Y)^{-2}$ wherein L is a metal of Group 1 or 2 of the Periodic Table of the Elements; X' independently is chloro, bromo, or iodo; x is 1 or 2, y is 1 or 2, and the product of x and y equals 2; and Cp*, Z, and Y are as previously defined.

Preferably, in the compounds of formulas $(Cp)_3MQ_nX_t$, $(Cp)_2MQ_nX_{t+1}$, or $CpMQ_nX_{t+2}$ n is 0 and t is 0 or 1. Exemplary of such compounds are tris($\eta^5$-cyclopentadienyl)titanium and tris($\eta^5$-cyclopentadienyl)titanium monohalide, bis($\eta^5$-cyclopentadienyl)titanium mono- and di-halides, bis ($\eta^5$-cyclopentadienyl)titanium mono- and di-alkoxides, ($\eta^5$-cyclopentadienyl)titanium di- and tri-halides, ($\eta^5$-cyclopentadienyl)titanium di- and tri-alkoxides, as well as the analoguous zirconium and hafnium compounds. Most preferably, in the above formulas both n and t are 0. Exemplary of neutral Lewis base-coordinated adducts of these compounds are the ether adducts of ($\eta^5$-cyclopentadienyl)titanium dihalides.

The process has been found especially suitable to prepare the bis(cyclopentadienyl) Group 4 metal complexes of formulas (II) and (IIa) wherein the metal is in the +3 oxidation state. More preferably, in the present process M is Ti(+3), n is 0, and t is 0. Most preferably, in the present process $(Cp)_3Ti$ or $(Cp)_2TiX$ is used wherein Cp is cyclopentadienyl and is $\eta^5$-bonded to titanium, and X is chloro.

Preferred examples of the dianionic salt compound corresponding to the formula: $(L^{+x})_y(Cp^*\text{-}Z\text{-}Y)^{-2}$ or $((LX')^{+x})_y(Cp^*\text{-}Z\text{-}Y)^2$ include: (tert-butylamido)(cyclopentadienyl)-1,2-ethanediyl dilithium or di(magnesiumchloride), (tertbutylamido)(tetramethylcyclopentadienyl)-1,2-ethanediyl dilithium or di(magnesiumchloride), (methylamido)(tetramethylcyclopentadienyl)-1,2-ethanediyl dilithium or di(magnesiumchloride), (methylamido)(cyclopentadienyl)-1,2-ethanediyl dilithium or di(magnesiumchloride), (methylamido) (ethylcyclopentadienyl)-1,2-ethanediyl dilithium or di(magnesiumchloride), (tert-butylamido) (cyclopentadienyl)dimethylsilane dilithium or di(magnesiumchloride), (tert-butylamido) (tetramethylcyclopentadienyl)dimethylsilane dilithium or di(magnesiumchloride), (tert-butylamido) (ethylcyclopentadienyl)dimethylsilane dilithium or di(magnesiumchloride), (methylamido) (tetramethylcyclopentadienyl)dimethylsilane dilithium or di(magnesiumchloride), (methylamido)(cyclopentadienyl) dimethylsilane dilithium or di(magnesiumchloride), (methylamido)(ethylcyclopentadienyl)dimethylsilane dilithium or di(magnesiumchloride), (phenylamido) (cyclopentadienyl)dimethylsilane dilithium or di(magnesiumchloride), (phenylamido) (tetramethylcyclopentadienyl)dimethylsilane dilithium or di(magnesiumchloride), (phenylamido)

(ethylcyclopentadienyl)dimethylsilane dilithium or di(magnesiumchloride), and the like.

The dianionic salt compounds used in the present process are known compounds and can be synthesized as described in EP-A-0,416,815 or U.S. Pat. No. 5,026,798.

In general, the bis(cyclopentadienyl) metal complexes of formula (II) and (IIa) can be prepared by contacting the compound of formulas $(Cp)_3MQ_nX_r$, $(Cp)_2MQ_nX_{r+1}$, or $CpMQ_nX_{r+2}$ with the dianionic salt compound in a suitable aprotic liquid diluent. The relative amounts of the compound of formulas $(Cp)_3MQ_nX_r$, $(Cp)_2MQ_nX_{r+1}$, or $CpMQ_nX_{r+2}$ and dianionic salt compound used may vary considerably, however, the best yields are generally obtained when using a stoichiometric molar quantity, or a slight stoichiometric molar excess of the dianionic salt compound. Preferably from 0.95 to 1.2 molar equivalents of the dianionic salt are used per molar equivalent of the coreactant, more preferably 1.0 to 1.1 molar equivalent.

Suitable aprotic organic solvents are hydrocarbons and ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and alkyl-substituted aromatic compounds such as benzene, toluene, xylene and the like, $C_{1-4}$ dialkyl ethers, $C_{1-4}$ dialkyl ether derivatives of (poly)alkylene glycols, and cyclic ether such as tetrahydrofuran. Mixtures of the foregoing are also suitable. More preferably the aprotic solvent is selected from the group consisting of ethers and aliphatic, cycloaliphatic, aromatic and alkyl-aromatic hydrocarbons, preferably $C_{5-10}$ hydrocarbons. Most preferably, the ether is diethyl ether or tetrahydrofuran.

The process to prepare the bis(cyclopentadienyl) metal complexes of formula (II) or (IIa) is usually conducted at a temperature from −78° C. to 150° C., preferably between −25° C. and 100° C., most preferably from 0° C. to 50° C. The time of reaction may vary from a few minutes to several days, but is generally a few hours.

The bis(cyclopentadienyl) metal complexes of formula (II) or (IIa) prepared according to the present process may be recovered or used as such in the process to prepare the bridged monocyclopentadienyl complexes of formula (I). When used as component in a catalyst system the bis(cyclopentadienyl) metal complexes of formula (II) are preferably recovered and purified. The recovery procedure for the bis(cyclopentadienyl) metal complexes involves separation from the resulting alkali metal or alkaline earth metal salt (LX and optionally LCp) and from the reaction medium. The separation of the byproduct salts from the desired product may occur by methods known to those skilled in the art, such as precipitation and filtration, extraction into a secondary solvent or other separation technique, depending of course on the differences between the solubility characteristics of both the desired product and byproduct salts. The recovery procedure is facilitated by the use of reaction media that are solvents for the resulting bridged monocyclopentadienyl complex but are non-solvents for the resulting byproducts, or vice versa. A preferred example of such a solvent in which the desired product is soluble, but the alkali metal or alkaline earth metal halidide or alkoxide salt is not, is hexane.

The bis(cyclopentadienyl) Group 4 metal complexes in the +3 and +4 oxidation states can be readily converted to one another by use of an appropriate oxidation agent, such as for example lead(II) chloride, or an appropriate reducing agent, such as for example magnesium metal.

According to a further aspect, the present invention provides novel bridged bis(cyclopentadienyl) Group 4 metal coordination complexes of formula (II) as previously defined herein. More preferably the bridged biscyclopentadienyl Group 4 metal coordination complexes correspond to formula (IIa) as previously defined herein.

Specific titanium(+3) complexes of formula (IIa) include: [(tert-butylamido)($\eta^5$-cyclopentadienyl)-1,2-ethanediyl] titanium $\eta^5$-cyclopentadienyl, [(tert-butylamido) (tetramethyl-$\eta^5$-cyclopentadienyl)-1,2ethanediyl]titanium $\eta^5$-cyclopentadienyl, [(tert-butylamido)(ethyl-$\eta^5$-cyclopentadienyl)-1,2-ethanediyl]titanium $\eta^5$-cyclopentadienyl, [(methylamido)(tetramethyl-$\eta^5$-cyclopentadienyl)-1,2-ethanediyl]titanium $\eta^5$-cyclopentadienyl, [(methylamido)($\eta^5$-cyclopentadienyl)-1,2-ethanediyl]titanium $\eta^5$-cyclopentadienyl, [(methylamido)(ethyl-$\eta^5$-cyclopentadienyl)-1,2-ethanediyl] titanium $\eta^5$-cyclopentadienyl, [(tert-butylamido)($\eta^5$-cyclopentadienyl)-1,2-ethanediyl]titanium pentamethyl-$\eta^5$-cyclopentadienyl, [(tert-butylamido)(tetramethyl-$\eta^5$-cyclopentadienyl)-1,2-ethanediyl]titanium pentamethyl-$\eta^5$-cyclopentadienyl, [(tert-butylamido)(ethyl-$\eta^5$-cyclopentadienyl)-1,2-ethanediyl]titanium pentamethyl-$\eta^5$-cyclopentadienyl, [(methylamido)(tetramethyl-$\eta^5$-cyclopentadienyl)-1,2-ethanediyl]titanium pentamethyl-$\eta^5$-cyclopentadienyl, [(methylamido)($\eta^5$-cyclopentadienyl)-1,2-ethanediyl]titanium pentamethyl-$\eta^5$-cyclopentadienyl, [(methylamido)(ethyl-$\eta^5$-cyclopentadienyl)-1,2-ethanediyl] titanium pentamethyl-$\eta^5$-cyclopentadienyl, [(phenylamido) (ethyl-$\eta^5$-cyclopentadienyl)-1,2-ethanediyl]titanium $\eta^5$-cyclopentadienyl, [(tert-butylamido)($\eta^5$-cyclopentadienyl)dimethylsilane]titanium $\eta^5$-cyclopentadienyl, [(tert-butylamido)(tetramethyl-$\eta^5$-cyclopentadienyl)dimethylsilane]titanium $\eta^5$-cyclopentadienyl, [(tert-butylamido)(ethyl-$\eta^5$-cyclopentadienyl)dimethylsilane]titanium $\eta^5$-cyclopentadienyl, [(methylamido)(tetramethyl-$\eta^5$-cyclopentadienyl)dimethylsilane]titanium $\eta^5$-cyclopentadienyl, [(methylamido)($\eta^5$-cyclopentadienyl) dimethylsilane]titanium $\eta^5$-cyclopentadienyl, [(methylamido)(ethyl-$\eta^5$-cyclopentadienyl)dimethylsilane] titanium $\eta^5$-cyclopentadienyl, [(tert-butylamido)($\eta^5$-cyclopentadienyl)dimethylsilane]titanium pentamethyl-$\eta^5$-cyclopentadienyl, [(tert-butylamido)(tetramethyl-$\eta^5$-cyclopentadienyl)dimethylsilane]titanium pentamethyl-$\eta^5$-cyclopentadienyl, [(tert-butylamido)(ethyl-$\eta^5$-cyclopentadienyl)dimethylsilane]titanium pentamethyl-$\eta^5$-cyclopentadienyl, [(methylamido)(tetramethyl-$\eta^5$-cyclopentadienyl)dimethylsilane]titanium pentamethyl-$\eta^5$-cyclopentadienyl, [(methylamido)($\eta^5$-cyclopentadienyl) dimethylsilane]titanium pentamethyl-$\eta^5$-cyclopentadienyl, [(methylamido)(ethyl-$\eta^5$-cyclopentadienyl)dimethylsilane] titanium pentamethyl-$\eta^5$-cyclopentadienyl, and the like.

Specific titanium(+4) complexes of formula (IIa) include: [(tert-butylamido)($\eta^5$-cyclopentadienyl)-1,2-ethanediyl] titanium (methyl) $\eta^5$-cyclopentadienyl, [(tert-butylamido) (tetramethyl-$\eta^5$-cyclopentadienyl)-1,2-ethanediyl]titanium (benzyl) $\eta^5$-cyclopentadienyl, [(methylamido)(tetramethyl-$\eta^5$-cyclopentadienyl)-1,2-ethanediyl]titanium ($\eta^5$-cyclopentadienyl) 2-(N,N-dimethylamino)benzyl, [(methylamido)($\eta^5$-cyclopentadienyl)-1,2-ethanediyl] titanium (methyl) $\eta^5$-cyclopentadienyl, [(methylamido) (ethyl-$\eta^5$-cyclopentadienyl)-1,2-ethanediyl]titanium (benzyl) ($\eta^5$-cyclopentadienyl , [(tert-butylamido)($\eta^5$-cyclopentadienyl)-1,2-ethanediyl]titanium ($\eta^5$-cyclopentadienyl)chloride, [(tert-butylamido)(tetramethyl-$\eta^5$-cyclopentadienyl)-1,2-ethanediyl]titanium ($\eta^5$- cyclopentadienyl)chloride, [(tert-butylamido)(ethyl-η⁵-cyclopentadienyl)-1,2-ethanediyl]titanium (η⁵-cyclopentadienyl)chloride, [(methylamido)(tetramethyl-η⁵-cyclopentadienyl)-1,2-ethanediyl]titanium (η⁵-cyclopentadienyl)chloride, [(phenylamido)(ethyl-η⁵-cyclopentadienyl)-1,2-ethanediyl]titanium (η⁵-cyclopentadienyl)chloride, [(tert-butylamido)(η⁵-cyclopentadienyl)-1,2-ethanediyl]titanium (methyl) pentamethyl-η⁵-cyclopentadienyl, [(phenylamido) (tetramethyl-η⁵-cyclopentadienyl)-1,2-ethanediyl]titanium (2-(dimethylphosphino)benzyl) η⁵-cyclopentadienyl, [(tert-butylamido)(ethyl-η⁵-cyclopentadienyl)-1,2-ethanediyl] titanium (benzyl) pentamethyl-η⁵-cyclopentadienyl, [(methylamido)(tetramethyl-η⁵-cyclopentadienyl)-1,2-ethanediyl]titanium (benzyl) pentamethyl-η⁵-cyclopentadienyl, [(methylamido)(ethyl-η⁵-cyclopentadienyl)-1,2-ethanediyl]titanium (methyl) pentamethyl-η⁵-cyclopentadienyl, [(tert-butylamido)(η⁵-cyclopentadienyl)-1,2-ethanediyl]titanium (pentamethyl-η⁵-cyclopentadienyl)chloride, [(tert-butylamido)(η⁵-cyclopentadienyl)-1,2-ethanediyl]titanium (η⁵-cyclopentadienyl)isopropoxide, [(tert-butylamido) (tetramethyl-η⁵-cyclopentadienyl)-1,2-ethanediyl]titanium (η⁵-cyclopentadienyl) n-butoxide, [(tert-butylamido)(η⁵-cyclopentadienyl)dimethylsilane]titanium (benzyl) η⁵-cyclopentadienyl, [(tert-butylamido)(tetramethyl-η⁵-cyclopentadienyl)dimethylsilane]titanium (benzyl) η⁵-cyclopentadienyl, [(tert-butylamido)(ethyl-η⁵-cyclopentadienyl)dimethylsilane]titanium (methyl) η⁵-cyclopentadienyl, [(methylamido)(ethyl-η⁵-cyclopentadienyl)dimethylsilane]titanium (methyl) η⁵-cyclopentadienyl, [(methylamido)(tetramethyl-η⁵-cyclopentadienyl)dimethylsilane]titanium (methyl) η⁵-cyclopentadienyl, [(methylamido)(η⁵-cyclopentadienyl) dimethylsilane]titanium (benzyl) η⁵-cyclopentadienyl, [(methylamido)(ethyl-η⁵-cyclopentadienyl)dimethylsilane] titanium (η⁵-cyclopentadienyl)chloride, [(tert-butylamido) (η⁵-cyclopentadienyl)dimethylsilane]titanium (η⁵-cyclopentadienyl)chloride, [(tert-butylamido)(tetramethyl-η5-cyclopentadienyl)dimethylsilane]titanium (η⁵-cyclopentadienyl) isopropoxide, [(tert-butylamido)(ethyl-η⁵-cyclopentadienyl)dimethylsilane]titanium (pentamethyl-η⁵-cyclopentadienyl) chloride, [(methylamido)(tetramethyl-η⁵-cyclopentadienyl)dimethylsilane]titanium (pentamethyl-η⁵-cyclopentadienyl) n-butoxide, [(methylamido)(η⁵-cyclopentadienyl)dimethylsilane]titanium (η⁵-cyclopentadienyl)chloride, [(tert-butylamido)(η⁵-cyclopentadienyl)dimethylsilane]titanium (η⁵-cyclopentadienyl) 2-(dimethylphosphino)benzyl, [(tert-butylamido)(tetramethyl-η⁵-cyclopentadienyl) dimethylsilane]titanium (η⁵-cyclopentadienyl) 2-(N,N-dimethylamino)benzyl, [(tert-butylamido)(tetramethyl-η⁵-cyclopentadienyl)dimethylsilane](cyclopentadienyl) titanium acetate, [(tert-butylamido)(tetramethyl-η⁵-cyclopentadienyl)dimethylsilane]titanium (cyclopentadienyl)(trimethylsiloxy), [(tert-butylamido) (tetramethyl-η⁵-cyclopentadienyl)dimethylsilane]titanium (cyclopentadienyl)trimethylsilyl, [(tert-butylamido) (tetramethyl-η⁵-cyclopentadienyl)dimethylsilane]titanium (pentadipentadienyl)trimethylsilylmethyl, [(tert-butylamido)(tetramethyl-η⁵-cyclopentadienyl) dimethylsilane]titanium(cyclopentadienyl)(ethylthiolate), [(tert-butylamido)(tetramethyl-η⁵-cyclopentadienyl) dimethylsilane]titanium (cyclopentadienyl)(methyl) and the like.

Other bis(cyclopentadienyl) Group 4 metal complexes of formulas (II) and (IIa) according to the present invention will, of course, be apparent to those skilled in the art.

Highly preferred complexes of formula (IIa) include: [(tert-butylamido)(tetramethyl-η⁵-cyclopentadienyl) dimethylsilane]titanium (cyclopentadienyl)chloride, [(tert-butylamido)(tetramethyl-η⁵-cyclopentadienyl) dimethylsilane]titanium (cyclopentadienyl), [(tert-butylamido)(tetramethyl-η⁵-cyclopentadienyl) dimethylsilane]titanium (cyclopentadienyl) bromide, [(tert-butylamido)(tetramethyl-η⁵-cyclopentadienyl) dimethylsilane]titanium (cyclopentadienyl)(methyl), [(tert-butylamido)(tetramethyl-η⁵-cyclopentadienyl) dimethylsilane]titanium (cyclopentadienyl)(2-(N,N-dimethylamino)benzyl), [(tert-butylamido)(tetramethyl-η⁵-cyclopentadienyl)dimethylsilane]titanium (cyclopentadienyl) (trimethylsilylmethyl), [(tert-butylamido)(tetramethyl-η⁵-cyclopentadienyl) dimethylsilane]titanium (cyclopentadienyl) (allyl), [(tert-butylamido)(tetramethyl-η⁵-cyclopentadienyl) dimethylsilane]zirconium (cyclopentadienyl) chloride, [(tert-butylamido)(tetramethyl-η⁵-cyclopentadienyl) dimethylsilane]zirconium (cyclopentadienyl)(2-(N,N-dimethylamino)benzyl).

The bis(cyclopentadienyl) Group 4 metal complexes corresponding to the formulas (II) and (IIa) can be prepared, for example, by contacting the corresponding bridged monocyclopentadienyl Group 4 metal halide or dihalide complex with L⁺ˣCp_y or (LX')⁺ˣCp_y, wherein L, X', x and y are as previously defined and x=y. This method, however, inherently has the disadvantages associated with the preparation of the bridged monocyclopentadienyl Group 4 metal halide or dihalide complexes as mentioned hereinbefore. A preferred method for preparing the novel bis(cyclopentadienyl) Group 4 metal .complexes of formulas (II) and (IIa) is described hereinbefore.

The bis(cyclopentadienyl) metal complexes of formula (II) or (IIa) may further be used, preferably in combination with an activating cocatalyst, in the addition polymerization of one or more addition polymerizable monomers. Exemplary of addition polymerizable monomers include ethylenically unsaturated monomers, for example olefins and more specifically α-olefins, conjugated or non-conjugated diolefins, acetylenically unsaturated monomers, and vinyl-aromatic monomers. In the present process one monomer can be polymerized or more than one different type of monomer can be interpolymerized. The term interpolymerization as used in the present application refers to a polymerization wherein at least two different monomers are used. These different monomers can be of the same type of monomer, such as α-olefins, for example ethylene and 1-octene, or from different types of monomers such as α-olefins and vinylaromatic monomers, for example ethylene and styrene, or α-olefins and diolefins. Preferably, the monomers have from 2 to 20 carbon atoms. Preferred monomers include the C_{2-10} α-olefins, especially ethylene, propylene, isobutylene, 1-butene, 1-hexene, 4-methyl-i-pentene, and 1-octene and mixtures thereof. Other preferred monomers include styrene, C_{1-4} alkyl substituted styrene, vinylbenzocyclobutene, ethylidenenorbornene and 1,4-hexadiene. The catalyst composition of the present invention comprises a bis(cyclopentadienyl) metal complex of formula (II) or (IIa) and an activating cocatalyst, such as an aluminoxane, or a cocatalyst capable of converting the complex of formula (II) or (IIa) to a cationic derivative or by a combination of the foregoing cocatalysts. A preferred technique is to employ as cocatalyst an aluminoxane or approximately stoichiometric amounts or slight excess of a strong Lewis acid activating agent, preferably tris (pentafluorophenyl)borane, or mixtures thereof. In general, the polymerization may be accomplished at conditions well known in the prior art for Ziegler-Natta or Kaminsky-Sinn type polymerization reactions, i.e., temperatures from 0° C.–250° C. and pressures from atmospheric to 1000 atmospheres. Suspension, solution, slurry, gas phase or other process conditions may be employed if desired. A support may be employed but preferably the catalysts are used in a homogeneous manner. Suitable cocatalysts and polymerization conditions are disclosed in U.S. application Ser. No. 545,403, filed Jul. 3, 1990 (EP-A-416,815), U.S. application Ser. No. 547,718 filed July 3, 1990 abandoned (EP-A-468, 651), U.S. application Ser. No. 702,475, filed May 20, 1991 abandoned (EP-A-516,828), U.S. application Ser. No. 876, 268, filed May 1, 1992 (EP-A-520,732), and U.S. application Ser. No. 8,003, filed Jan. 21, 1993 (WO 92/19104), as well as U.S. Pat. Nos. 5,055,438, 5,057,475, 5,096,867, 5,064,802 and 5,132,380, all of which are incorporated herein by reference.

In most polymerization reactions the equivalent ratio of catalyst:polymerizable compound employed is from $10^{-12}:1$ to $10^{-1}:1$, more preferably from $10^{-8}:1$ to $10^{-5}:1$.

Having described the invention the following examples are provided as further illustration thereof and are not to be construed as limiting. Unless stated to the contrary all parts and percentages are expressed on a weight basis. All metal complex preparations were performed under an inert atmosphere of argon or nitrogen.

PART A: Preparation of Complexes of Formula (IIa)

EXAMPLE 1

[(N-tert-butylamido)dimethyl(tetramethyl-$\eta^5$-cyclopentadienyl)silane]titanium(+3) (cyclopentadienyl)

Preparation A:

1.911 g (3.71 mmol) of $(MgCl.THF)_2$ $(C_5Me_4SiMe_2NCMe_3)$ (prepared according to EP-A-514, 828) and 1.380 g (3.72 mmol) of $TiCl_3(THF)_3$ (prepared according to Inorg. Syn. 1982, 21, 135) were combined in a flask with 70 mL of THF to give a dark solution. After stirring for 5 minutes, 2.07 mL (3.73 mmol) of 1.80M sodium cyclopentadienide solution in THF was added. The resulting pale yellow solution was stirred for 16 hours. The solvents were removed under reduced pressure. The residue was extracted with pentane, filtered and concentrated. After chilling for 16 hours at –40° C. a yellow-green microcrystalline product was collected on a frit and dried under reduced pressure. The yield of [(N-tert-butylamido)dimethyl (tetramethyl-$\eta^5$-cyclopentadienyl)silane]titanium(+3) (cyclopentadienyl) (A) was 1.047 g, 77.6 percent.

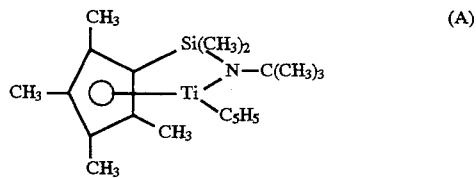

(A)

The ESR (Electron Spin Resonance) spectrum of this material exhibited two lines at room temperature centered at g=1.973. The product's identity was confirmed by reaction with lead(+2)chloride as in Example 2, Preparation B to give [(N-tert-butylamido)dimethyl(tetramethyl-$\eta^5$-cyclopentadienyl)silane](cyclopentadienyl)titanium(+4) chloride.

Preparation B:

0.0987 g (0.248 mmol) of [(N-tert-butylamido)dimethyl (tetramethyl-$\eta^5$-cyclopentadienyl)silane](cyclopentadienyl) titanium(+4)chloride as prepared in Example 2, Preparation A and 0.012 g (0.49 mmol) magnesium granules were stirred overnight in 5 ml THF. The originally red-orange solution turned olive green. The solvent was removed under reduced pressure. The residue was extracted with pentane, the solution was filtered and the solvent was removed under reduced pressure. The yield of the yellow-green product (A) was 0.0825 g, 91.8%.

Preparation C:

1.6744 g (3.26 mmol) of $(MgCl.THF)_2$ $(C_5Me_4SiMe_2NCMe_3)$ and 0.600 g (3.26 mmol) of cyclopentadienyltitanium(+3) dichloride (prepared according to Aust. J. Chem. 1971, 24, 2533–2540) were combined in a flask with 35 ml THF. After stirring overnight, the solvents were removed under reduced pressure from the green solution. The residue was extracted with pentane, filtered and concentrated to give the product (A) as a yellow-green powder. The yield was 0.691 g, 58.4%.

Preparation D:

1.016 g (4.76 mmol, based on the monomer) of [$(C_5H_5)_2TiCl]_2$ (prepared as in Inorg. Chem., 1975, 14, 2192) and 2.442 g (4.76 mmol) $(MgCl.THF)_2(C_5Me_4SiMe_2NCMe_3)$ were combined in a flask with 70 ml THF. The green reaction mixture was stirred overnight. The solvent was removed under reduced pressure, the residue was extracted with toluene and the resulting solution was filtered. Several milliliters of 1,4-dioxane were added. The precipitated solids were filtered off and the solvent was removed. A small portion (0.156 g) of the green solid was removed and reacted with $PbCl_2$ as in Example 2, Preparation B to form (B) in 98.2% yield. The remaining green solid was extracted with pentane and the solution was filtered from a small amount of grey-white powder. The solvent was concentrated, the product was recrystallized twice from pentane in the freezer. The total yield of (A) was 1.332 g, 77.2%.

Preparation E:

Powdered $(C_5Me_4SiMe_2NCMe_3)(MgCl.THF)_2$ (0.5309 g, 1.03 mmol) was added to a solution of 0.2496 g (1.03 mmol) $(C_5H_5)_3Ti$ (prepared according to Aust. J. Chem., 1968, 21, 807–810) in 25 mL THF. The deep green solution immediately turned a lighter olive green. The reaction mixture was stirred overnight. The solution was filtered and the solvent was removed under vacuum. The residue was extracted with toluene, then filtered and the solvent was removed under vacuum. The residue was extracted with hexane, then filtered and the solvent was removed under vacuum. The pale green solid was slurried in a small amount of hexane, then filtered off and dried under vacuum. The yield of yellowish green product was 0.3717 g, 99.9%. The product was identified as product (A), as follows. A small amount (about 0.015 g) of the product (A) was oxidized in $C_6D_6$ in an NMR tube by shaking with excess $PbCl_2$ to give $(C_5Me_4SiMe_2NCMe_3)TiCl(C_5H_5)$ which was identified by its $^1H$ and $^{13}C$ NMR spectra. No other Cp-containing products were present.

EXAMPLE 2

[(N-tert-butylamido)dimethyl(tetramethyl-$\eta_5$-cyclopentadienyl)silane]titanium(+4) (cyclopentadienyl)chloride Preparation A:

To a solution of 0.5577 g (1.51 mmol) of $(C_5Me_4SiMe_2NCMe_3)TiCl_2$ (prepared according to EP-A-416,815) in 20 ml THF was slowly added 0.841 ml of 1.8M (0.151 mmol) sodium cyclopentadienide in THF. The reaction mixture was heated gently. The color turned deep red within a short time. After stirring overnight the solvent was removed under reduced pressure. The very dark red residue was extracted with pentane, the solution was filtered and the solvent was removed under reduced pressure. The crude product was recrystallized from 2 ml pentane at −40° C. The red product [(N-tert-butylamido)dimethyl(tetramethyl-$\eta^5$-cyclopentadienyl)silane]titanium(+4)(cyclopentadienyl) chloride (B) was dried under reduced pressure. The yield was 0.5248 g, 87.1%. The structure was confirmed by NMR: $^1$H NMR ($C_6D_6$) δ 5.86 (s, 5H), 2.48 (s, 3H), 1.82 (s, 3H), 1.77 (s, 3H), 1.59 (s, 3H), 1.35 (s, 9H), 0.61 (s, 3H), 0.25 (s, 3H). $^{13}$C NMR ($C_6D_6$) δ 137.7, 135.5, 129.6, 125.4, 114.3, 109.4, 63.7, 34.2, 16.8, 15.1, 12.9, 12.8, 9.7, 6.1.

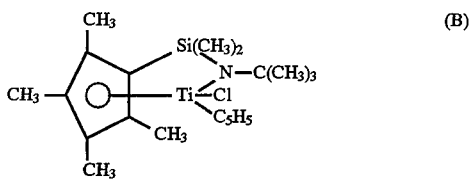

(B)

Preparation B:

In a flask were combined 0.700 g (1.93 mmol) of product (A) as prepared in Example 1 and 0.282 g (1.01 mmol) lead(II)chloride with 30 ml toluene. The resulting deep red solution was stirred for three hours, then filtered from metallic lead and the solvent was removed under reduced pressure. The red crystalline product was washed with 2 ml cold pentane, then dried under reduced pressure. The yield of product (B) was 0.7455 g, 97%.

Preparation C:

1.500 g (2.92 mmol) of $(MgCl.THF)_2$ $(C_5Me_4SiMe_2NCMe_3)$ and 0.6411 g (2.92 mmol) of cyclopentadienyl titanium trichloride (prepared according to J. Am. Chem. Soc. 1958, 80, 4744) were combined in a flask with 35 ml THF. After stirring overnight, the solution was filtered and the solvent was removed under reduced pressure. The residue was extracted with pentane, filtered and concentrated until the solid began to form. After chilling to −35° C., the solids were collected on a filter, washed twice with 2 ml cold pentane, then dried under reduced pressure to give the product (B) as a red powder. The yield was 0.6369 g, 54.8%.

Preparation D:

1.0185 g (4.09 mmol) of bis(cyclopentadienyl)titanium dichloride (purchased from Aldrich) and 2.099 g (4.09 mmol) $(MgCl.THF)_2(C_5Me_4SiMe_2NCMe_3)$ were combined in a flask with 50 ml THF to form a dark green reaction mixture. After stirring overnight, the resulting mixture had turned brownish red, and the solvent was removed under reduced pressure. The residue was extracted with toluene, then filtered and the solvent was removed under reduced pressure. The residue was extracted with pentane and the red solution was filtered from a grey solid. The solvent was removed to give an impure brick-red solid. 1 to 2 ml of 1,4-dioxane were added to a benzene/toluene solution of the red solid, then the solvent was removed. The residue was extracted with pentane and the solution was filtered from a small amount of grey powder. The product was recrystallized twice from pentane in the freezer. The yield of product (B) was 0.5077 g, 31.2%.

Preparation E:

Powdered $(C_5Me_4SiMe_2NCMe_3)(MgCl.THF)_2$ (0.6358 g, 1.23 mmol) was added to a solution of 0.2642 g (1.23 mmol) $(C_5H_5)TiCl_2(OCH_3)$ (prepared by reaction of $(C_5H_5)TiCl_3$ with $NaOCH_3$ in 30 ml THF. The color immediately changed from lemon yellow to deep brownish-red. The reaction mixture was stirred for two days. The solvent was removed under vacuum and the residue was extracted with hexane, then filtered. The solution was concentrated and placed in a freezer at −35° C. The product was collected on a frit and Washed with 3×2 ml portions of cold hexane. The orange powder was dried under vacuum. The product was identified by $^1$H NMR spectroscopy as the title compound with none of the methoxy analogue present. The yield was 0.1556 g, 31.8%.

Preparation F:

Powdered $(C_5Me_4SiMe_2NCMe_3)(MgCl.THF)_2$ (0.6644 g, 1.28 mmol) was added to a solution of 0.3502 g (1.28 mmol) $(C_5H_5)_2TiCl(OCH(CH_3)_2)$ (preparation analogous to the procedure for $(C_5H_5)_2TiCl(OC_2H_5)$ in J. Am. Chem. Soc. 1980, 102, 3009–3014) in 25 ml THF. The bright orange solution immediately turned deep brownish-red. The reaction mixture was stirred for two days. The solvent was removed under vacuum and the residue was extracted with toluene, then filtered and the solvent was removed under vacuum. The residue was extracted with hexane, filtered and recrystallized in the freezer. The yield of red-orange product, identified by $^1$H and $^{13}$C NMR as (B), was 0.3800 g, 74.3%, with none of the isopropoxy analogue being present.

EXAMPLE 3

[(N-tert-butylamido)dimethyl(tetramethyl-$\eta^5$-cyclopentadienyl)silane]zirconium (cyclopentadienyl)chloride To a solution of 0.8286 g (2.01 mmol) $(C_5Me_4SiMe_2NCMe_3)ZrCl_2$ (prepared according to EP-A 416,815) in 60 ml ether was slowly added 1.12 ml of 1.8M (2.02 mmol) sodium cyclopentadienide in THF. The reaction mixture was stirred for several days, then filtered and the solvent was removed. The colorless solid was slurried in pentane, chilled in a freezer, collected on a filter, washed twice With 2 ml cold pentane, then dried under reduced pressure. The yield of the product $(C_5Me_4SiMe_2NCMe_3)ZrCl(C_5H_5)$ was 0.7270 g, 81.8%. $^1$H NMR ($C_6D_6$) δ 5.97 (s, 5H), 2.36 (s, 3H), 1.85 (s, 3H), 1.81 (s, 3H), 1.67 (s, 3H), 1.29 (s, 9H), 0.61 (s, 3H), 0.38 (s, 3H). $^{13}$C NMR ($C_6D_6$) δ 132.7, 130.2, 126.1, 122.9, 112.9, 106.2, 57.7, 35.2, 15.6, 14.5, 12.3, 12.2, 10.1, 6.7.

PART B: Preparation of Complexes of Formula (I)

EXAMPLE 4

[(N-tert-butylamido)dimethyl(tetramethyl-$\eta^5$-cyclopentadienyl)silane]titanium(+3) 2-(N,N-dimethylamino)benzyl To a solution of 0.2361 g (0.651 mmol) of (A), as prepared in Example 1, in 12 ml of diethyl ether was slowly added 0.0919 g (0.651 mmol) of powdered 2-(N,N-dimethylamino)benzyl lithium, prepared by reaction of butyl lithium with N,N-dimethyl-o-toluene, accompanied by stirring. A color change was apparent within 1 hour. After 48 hours the solution was filtered to remove lithium cyclopentadienide (0.0458 g, 97.6%). The solvent was removed under reduced pressure from the dark reddish brown solution. The yield of red-brown product was 0.2801 g, 99.6 percent.

The product's identity as [(N-t-butylamido)dimethyl (tetramethyl-$\eta^5$-cyclopentadienyl) silane]titanium(+3) 2-(N, N-dimethylamino)benzyl (C) was confirmed by its reaction with lead(+2) chloride. A solution of (C) in $C_6D_6$ was placed in an NMR tube. Excess lead(II) chloride was added and the sample was shaken. The red-brown solution turned yellow-orange-brown. The excess lead(+2) chloride and lead metal which formed were tipped away from the solution. The $^1$H NMR showed the product to be [(N-t-butylamido)dimethyl(tetramethyl-$\eta^5$-cyclopentadienyl)silane]titanium(+4) 2-(N,N-dimethylamino)benzyl chloride by comparison with an authentic sample which was prepared by reaction of (C$_5$Me$_4$SiMe$_2$NCMe$_3$)TiCl$_2$ with 2-(N,N-dimethylamino)benzyl lithium as described in WO 93/19104. $^1$HNMR (C$_6$D$_6$) 7.00 (m, 1H), 6.92 (m, 1H), 6.78 (m, 2H), 2.77 (s, 1H), 2.73 (s, 1H), 2.52 2.27 (s, 3H), 2.03 (s, 3H), 1.90 (s, 3H), 1.57 (s, 9H), 1.01 (s, 3H), 0.57 (s, 3H), 0.50 (s, 3H).

EXAMPLE 5

[(N-tert-butylamido)dimethyl(tetramethyl-$\eta^5$-cyclopentadienyl)silane]titanium(+4) bis(2-(N,N-dimethylamino)benzyl)

To a –35° C. solution of 0.2134 g (0.536 mmol) of product (B), as prepared in Example 2, in 25 ml diethyl ether was slowly added 0.0757 g (0.536 mmol) of powdered 2-(N,N-dimethylamino)benzyl lithium accompanied by stirring. After allowing to warm to room temperature and stirring overnight, the color of the solution was reddish orange. $^1$H NMR analysis of this intermediate product shows the absence of both the starting material and the chloro complex (C$_5$Me$_4$SiMe$_2$NCMe$_3$)Ti(CH$_2$C$_6$H$_4$(o-NMe$_2$))Cl (by comparison with an authentic sample prepared by reaction of (C$_5$Me$_4$SiMe$_2$NCMe$_3$)TiCl$_2$ with LiCH$_2$C$_6$H$_4$(o-NMe$_2$). The $^1$H NMR spectrum of the compound is consistent with a structure corresponding to (C$_5$Me$_4$SiMe$_2$NCMe$_3$)Ti(CH$_2$C$_6$H$_4$(o-NMe$_2$))Cp. A second equivalent of the lithium reagent was added (total 0.1514 g, 1.072 mmol) to the reaction mixture. The reaction mixture was stirred overnight, then the solvent was removed under reduced pressure from the dark reddish brown solution. The residue was extracted with pentane, the solution was filtered and the solvent was removed. The yield of the red-brown product (D) was 0.2778 g, 91.6%. $^1$H NMR (C$_6$D$_6$) (C$_5$Me$_4$SiMe$_2$NCMe$_3$)Ti(CH$_2$C$_6$H$_4$(o-NMe$_2$))Cp: δ 7.22 (m, 1H), 7.08 (m, 2H), 7.07 (m, 5.78 (s, 5H), 2.58 (s, 6H), 2.4 (br, 2H), 2.15 (s, 1.82, (s, 3H), 1.62 (s, 3H), 1.46, (s, 3H), 1.35 (s, 9H), 0.71 (s, 3H), 0.67, (s, 3H) (C$_5$Me$_4$SiMe$_2$NCMe$_3$)Ti(CH$_2$C$_6$H$_4$(o-NMe$_2$))$_2$: $^1$H NMR (C$_6$D$_6$) δ 7.1 (br, 2H), 6.95 (br, 6H), 2.70 (d, 2H, J=9.34 Hz), 2.49 (br s with shoulders, 14H), 1.87 (s, 6H), 1.85 (s, 6H) 1.50 (s, 9H), 0.51 (s, 6H). $^{13}$C NMR 149.1, 145.7, 133.7, 131.4, 129.4, 123.5, 123.2, 119.3, 100.5, 80.1, 60.0, 44.7, 34.1, 14.9, 11.6, 6.6.

EXAMPLE 6

[(N-tert-butylamido)dimethyl(tetramethyl-$\eta^5$-cyclopentadienyl)silane]titanium(+4) dimethyl To a –35° C. solution of 0.2099 g (0.527 mmol) of product (B), as prepared in Example 2, in 25 ml diethyl ether was slowly added 0.595 ml of 1.012M (0.602 mmol) methyl lithium in solution in ether. The reaction mixture was allowed to warm to room temperature during which time the color changed from red-orange to greenish-yellow. After stirring overnight, the reaction mixture was shown by $^1$H NMR to consist of a 6:1 ratio of the bis(cyclopentadienyl) monomethyl derivative and the monocyclopentadienyl dimethyl derivative. The remainder of the second equivalent of methyl lithium was added (total 1.04 ml, 1.052 mmol) to the reaction mixture and the reaction mixture was stirred overnight. The solvent was removed under reduced pressure, the residue was extracted with pentane, and the solution was filtered. The solvent was concentrated until crystals began to form, and then was chilled in the freezer. The supernatant was decanted and the solid was dried under vacuum to give 0.1611 g, 93.3% of light yellow product which was identified by $^1$H NMR spectroscopy to be [(N-tert-butylamido)dimethyl(tetramethyl-$\eta^5$-cyclopentadienyl)silane]titanium (+4) dimethyl (Product E). $^1$H NMR (C$_6$D$_6$) (C$_5$Me$_4$SiMe$_2$NCMe$_3$)Ti(C$_5$H$_5$)Me: δ 5.66 (s, 5H), 2.22 (s, 3H), 1.82 (s, 3H), 1.56 (s, 3H), 1.42 (s, 3H), 1.26 (s, 9H), 0.58 (s, 3H), 0.46 (s, 3H), 0.19 (s, 3H); (C$_5$Me$_4$SiMe$_2$NCMe$_3$)TiMe$_2$: δ 1.97 (s, 6H), 1.86 (s, 6H), 1.57 (s, 9H), 0.51 (s, 6H), 0.43 (s, 6H).

PART C: Polymerization Using Complex of Formula (II)

EXAMPLE 7

A thermostat-controlled continuously-stirred 2 l reactor charged with 740 g Isopar E™ (available from Exxon Chemical) and 118 g 1-octene was pressurized with 25 psi hydrogen and 450 psi ethylene and heated to 120° C. 10.0 μmol [(N-tert-butylamido)dimethyl(tetramethyl-$\eta$5-cyclopentadienyl)-silane](cyclopentadienyl)zirconium chloride (prepared according to Example 3) were combined with 5000 μmol (based on the AlCH$_3$O empirical formula) MMAO (triisobutylaluminum-modified methylaluminoxane) and then added to the reactor. An exotherm of 35° C. was observed. After a reaction time of 15 minutes, the polymer solution was removed from the reactor and the solvent was removed. The yield of polymer was 138.8 g.

EXAMPLE 8

Example 7 was repeated, except that 2 μmol zirconium complex and 1000 pmol MMAO were used. An exotherm of 8.2° C. was observed. The polymer yield was 89.4 g.

EXAMPLE 9

Example 8 was repeated, except that the reaction temperature was 140° C. and 650 g Isopar E and 208 g 1-octene were used. An exotherm of 4.7° C. was observed. The polymer yield was 53.4 g.

EXAMPLE 10

Example 7 was repeated, except that 10.0 μmol [(N-tert-butylamido)dimethyl(tetramethyl-$\eta^5$-cyclopentadienyl)silane](cyclopentadienyl)titanium chloride (B) were used instead of the zirconium complex. An exotherm of 0.8° C. was observed. The polymer yield was 2.0 g.

EXAMPLE 11

Example 10 was repeated twice, except that 10.0 pmol [(N-tert-butylamido)dimethyl(tetramethyl-$\eta^5$-cyclopentadienyl)silane](cyclopentadienyl)titanium (A) were used instead of (B). Exotherms of 0.8° C. and 0.6° C. were observed in each case. The polymer yield in each case was 6.6 g.

What is claimed is:

1. A bis(cyclopentadienyl) Group 4 metal complex corresponding to the formula:

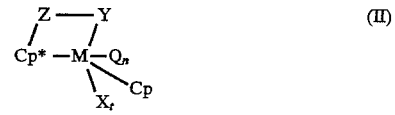

(II)

wherein:

Cp* is a cyclopentadienyl group or a substituted derivative of said cyclopentadienyl group wherein the substituent is hydrocarbyl, silyl, amino, aminohydrocarbyl, halo, halohydrocarbyl, silylhydrocarbyl, hydrocarbylmetalloid or halohydrocarbylmetalloid, or adjacent substituents on Cp* may be linked together, said Cp* being covalently bonded to Z and π-bonded to M and containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms and being covalently bonded to Y and CD*, with the proviso that when M is zirconium then Z is not 1,2-ethene-diyl or 1,3-propane-diyl;

Y is a linking group comprising nitrogen or phosphorus covalently bonded to M and Z through said nitrogen or phosphorus atom;

M is a metal of Group 4 of the Periodic Table of the Elements in an oxidation state of +3 or +4;

X independently each occurrence is halo, hydrocarbyloxy, siloxy, carboxy, sulfido or sulfonato;

Cp independently is a cyclopentadienyl group or a substituted derivative of said cyclopentadienyl group wherein the substituent is hydrocarbyl, silyl, halo, amino, aminohydrocarbyl, halohydrocarbyl, silylhydrocarbyl, hydrocarbylmetalloid or halohydrocarbylmetalloid or adjacent substituents in the Cp may be linked together, said Cp being π-bonded to M, and containing up to 50 nonhydrogen atoms;

Q independently each occurrence is hydride, or a monovalent anionic ligand selected from the group consisting of hydrocarbyl, silyl, amido and phosphido groups, said groups optionally being further substituted with one or more amino, phosphino, ether, ester, thioether, or silyl groups, said Q having up to 50 nonhydrogen atoms, provided that Q is not a cyclopentadienyl or substituted cyclopentadienyl group;

n is 0 or 1; t is 0 or 1; and the sum of n and t is three less than the oxidation state of M.

2. A bis(cyclopentadienyl) Group 4 metal complex according to claim 1 and corresponding to the formula:

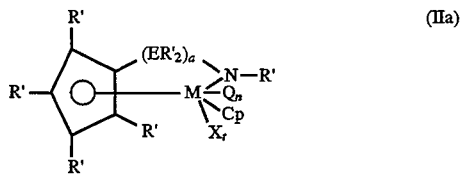

(IIa)

wherein:

R' each occurrence is independently selected from the group consisting of hydrogen, silyl, hydrocarbyl, and silyl-substituted hydrocarbyl, said R' having up to 10 carbon or silicon atoms or two such R' groups together are a $C_3$ or $C_4$ hydrocarbylene moiety forming a fused ring with adjacent carbons of the cyclopentadienyl group;

E independently each occurrence is silicon or carbon;

Q is allyl, alkyl-substituted allyl, pentadienyl, alkyl-substituted pentadienyl, or an alkyl, aryl, aralkyl, silyl, trialkylsilylalkyl, or dialkylaminoaralkyl group, said group having up to 10 carbons;

X and Cp are as defined in claim 1; M is titanium or zirconium in an oxidation state of +3 or +4;

a is 1 or 2; t is 0 or 1; n is 0 or 1; and the sum of n and t is three less than the oxidation state of titanium.

3. A bis(cyclopentadienyl) Group 4 metal complex according to claim 2 and selected from the group consisting of [(N-tert-butylamido)dimethyl(tetramethyl-η⁵-cyclopentadienyl)silane]titanium(cyclopentadienyl) chloride, [(N-tert-butylamido)dimethyl(tetramethyl-η⁵-cyclopentadienyl)silane]titanium(cyclopentadienyl), [(N-tert-butylamido)dimethyl(tetramethyl-η⁵-cyclopentadienyl)silane]titanium(cyclopentadienyl)bromide, [(N-tert-butylamido)dimethyl(tetramethyl-η⁵-cyclopentadienyl)silane]titanium(cyclopentadienyl)methyl, [(N-tert-butylamido)dimethyl(tetramethylη⁵-cyclopentadienyl)silane]titanium(cyclopentadienyl)(2-(N,N-dimethylamino)benzyl), [(N-tert-butylamido)dimethyl(tetramethyl-η⁵-cyclopentadienyl)silane]titanium(cyclopentadienyl)trimethylsilylmethyl, [(N-tert-butylamido)dimethyl(tetramethyl-η⁵-cyclopentadienyl)silane]titanium(cyclopentadienyl)allyl, [N-tert-butylamido)dimethyl(tetramethyl-η⁵-cyclopentadienyl)silane]titanium(cyclopentadienyl)(benzyl), [(N-tert-butylamido)dimethyl(tetramethyl-η⁵-cyclopentadienyl)silane]zirconium(cyclopentadienyl) chloride, [(N-tert-butylamido)dimethyl(tetramethyl-η⁵-cyclopentadienyl)silane]zirconium(cyclopentadienyl)(2-(N,N-dimethylamino)benzyl), [(N-tert-butylamido)dimethyl(tetramethyl-η⁵-cyclopentadienyl)silane]zirconium (cyclopentadienyl)(methyl).

4. A process for preparing bis(cyclopentadienyl) Group 4 metal complexes corresponding to the formula:

(II)

wherein:

Cp* is a cyclopentadienyl group or a substituted derivative of said cyclopentadienyl group wherein the substituent is hydrocarbyl, silyl, amino, aminohydrocarbyl, halo, halohydrocarbyl, silylhydrocarbyl, hydrocarbylmetalloid or halohydrocarbylmetalloid, or adjacent substituents on Cp* may be linked together, said Cp* being covalently bonded to Z and π-bonded to M and containing up to 50 nonhydrogen atoms;

Z is a divalent moiety comprising oxygen, nitrogen, phosphorous, boron, or a member of Group 14 of the Periodic Table of the Elements, said moiety having up to 30 nonhydrogen atoms and being covalently bonded to Y and Cp*;

Y is a linking group comprising nitrogen, phosphorus, oxygen or sulfur covalently bonded to M and Z through said nitrogen, phosphorus, oxygen or sulfur atom;

M is a metal of Group 4 of the Periodic Table of the Elements in an oxidation state of +3 or +4;

Q independently each occurrence is hydride, or a monovalent anionic ligand selected from the group consisting of hydrocarbyl, silyl, amido and phosphido groups, said groups optionally being further substituted with one or more amino, phosphino, ether, ester, thioether, or silyl groups, said Q having up to 50 nonhydrogen atoms, provided that Q is not a cyclopentadienyl or substituted cyclopentadienyl group;

Cp independently is a cyclopentadienyl group or a substituted derivative of said cyclopentadienyl group wherein the substituent is hydrocarbyl, silyl, halo, amino, aminohydrocarbyl, halohydrocarbyl, silylhydrocarbyl, hydrocarbylmetalloid or halohydrocarbylmetalloid, or adjacent substituents in the Cp may be linked together, said Cp being π-bonded to M, and containing up to 50 nonhydrogen atoms;

X independently each occurrence is halo, hydrocarbyloxy, siloxy, carboxy, sulfido or sulfonato;

n is 0 or 1; t is 0 or 1; and the sum of n and t is three less than the oxidation state of M;

the process comprising contacting in an aprotic organic solvent: i) a compound corresponding to one of the formulas $(Cp)_3MQ_nX_t$, $(Cp)_2MQ_nX_{t+1}$, or $CpMQ_nX_{t+2}$ or a neutral Lewis base coordinated adduct thereof, wherein n is 0 or 1; t is 0 or 1; the sum of n and t is three less than the valence of M; and Cp, M, Q and X are as previously defined; and ii) a dianionic salt compound corresponding to the formula: $(L^{+x})_y(Cp\text{*-}Z\text{-}Y)^{-2}$ or $((LX')^{+x})_y(Cp\text{*-}Z\text{-}Y)^{-2}$ wherein L is a metal of Group 1 or 2 of the Periodic Table of the Elements; X' independently is chloro, bromo, or iodo; x is 1 or 2, y is 1 or 2, and the product of x and y equals 2; and Cp*, Z, and Y are as previously defined; to form the complex of formula (II).

5. A process according to claim 4 wherein n is 0 and t is 0 or 1.

6. A process according to claim 5 wherein t is 0.

7. A process according to claim 4 conducted at a temperature of from −78° C. to 150° C.

8. A process according to claim 4 wherein the aprotic organic solvent is selected from the group consisting of ethers and aliphatic, cycloaliphatic, aromatic and alkylaromatic hydrocarbons.

* * * * *